United States Patent [19]

Pioch et al.

[11] 3,962,257

[45] June 8, 1976

[54] 3-PHENACYLPIPERIDINES

[75] Inventors: Richard P. Pioch; Klaus K. Schmiegel, both of Indianapolis, Ind.

[73] Assignee: Eli Lilly and Company, Indianapolis, Ind.

[22] Filed: May 31, 1974

[21] Appl. No.: 475,219

[52] U.S. Cl............................. 260/293.8; 260/293.51; 260/293.73; 260/293.75; 260/293.76; 424/267
[51] Int. Cl.²................................. C07D 211/32
[58] Field of Search....... 260/293.8, 293.73, 293.75, 260/293.76

[56] References Cited
FOREIGN PATENTS OR APPLICATIONS
40,778   6/1973   Japan.............................. 260/293.8
40,779   6/1973   Japan.............................. 260/293.8

OTHER PUBLICATIONS

Synthetic Organic Chemistry, (1953) Wagner et al., pp. 332–333.
C.A. 64: 15856b (1966) Hoffman La Roche & Co.
Rec. Trav. Chim., 82: 763–772, (1963) Noordwijk et al.

*Primary Examiner*—Sherman D. Winters
*Attorney, Agent, or Firm*—William E. Maycock; Everet F. Smith

[57] ABSTRACT

3-Phenacylpiperidines, useful as depressants, stimulants, and anti-inflammatory agents, are obtained by preparing, from a 3-halomethylpiperidine, a 3-piperidylmethylmagnesium halide which is condensed with a benzonitrile.

6 Claims, No Drawings

3-PHENACYLPIPERIDINES

BACKGROUND OF THE INVENTION

The present invention relates to 3-phenacylpiperidines. More particularly, the present invention relates to 3-phenacylpiperidines, useful as central nervous system depressants and stimulants, and also as anti-inflammatory agents, which are obtained by preparing, from a 3-halomethylpiperidine, a 3-piperidylmethylmagnesium halide which is condensed with a benzonitrile.

Central nervous system depressants are widely used, especially in the treatment of such psychosis-induced symptoms as moderate to severe agitation, anxiety, and tension, assaultiveness, delusions, hallucinations, hostility, and hyperactivity. Among the more common depressants are the phenothiazines and the butyrophenones (the rauwolfia alkaloids having been largely supplanted by the phenothiazines). Both groups of compounds, however, possess undesirable side effects. For example, the phenothiazines exhibit hypersensitivity reactions, extrapyramidal effects, orthostatic hypotension, metabolic effects, and an interaction with other drugs. The butyrophenones exhibit extrapyramidal effects, drug interaction, metabolic effects, blood dyscrasias, and transient hypotension.

Central nervous system stimulants, such as the amphetamines, frequently find use in the treatment of minimal brain dysfunction in children, e.g., hyperkinetic behavior disorders, and in the treatment of narcolepsy. However, stimulants such as the amphetamines suffer from undesirable side effects, the most serious of which are drug dependence and manifestations of chronic intoxication.

Mammals, both humans and animals, are known to suffer from various conditions involving inflammation with concomitant swelling, tenderness, decreased mobility, pain, and fever. While a number of anti-inflammatory agents are effective in the symptomatic treatment of such inflammatory conditions as rheumatoid arthritis, rheumatoid spondylitis, osteoarthritis, degenerative joint diseases, and the like, such agents have a number of undesirable side effects, such as gastric irritation and the like.

SUMMARY OF THE INVENTION

It therefore is an object of the present invention to provide novel 3-phenacylpiperidines which are useful in at least one of the above-described areas.

It also is an object of the present invention to provide a process for preparing said 3-phenacylpiperidines.

These and other objects will be apparent to those skilled in the art from a consideration of the specification and claims which follow.

In accordance with the present invention, novel 3-phenacylpiperidines are provided which have the following general formula:

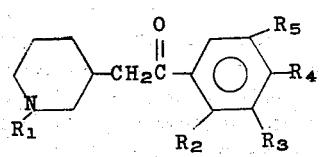

wherein $R_1$ is selected from the group consisting of hydrogen, $C_1$-$C_3$ alkyl, allyl, cyano, and carbamoyl; at least two of $R_2$, $R_3$, $R_4$, and $R_5$ must be hydrogen; when two of $R_2$, $R_3$, $R_4$, and $R_5$ are hydrogen, $R_2$ is either hydrogen or chloro, and when three of $R_2$, $R_3$, $R_4$, and $R_5$ are hydrogen, $R_2$ is selected from the group consisting of hydrogen, fluoro, chloro, methyl, and trifluoromethyl; $R_3$ and $R_5$ independently are selected from the group consisting of hydrogen, fluoro, chloro, methyl, and trifluoromethyl; and $R_4$ is selected from the group consisting of hydrogen, fluoro, chloro, methyl, trifluoromethyl, and, when three of $R_2$, $R_3$, $R_4$, and $R_5$ are hydrogen, methoxy and methylthio; and the pharmaceutically-acceptable acid addition salts of basic members thereof.

When $R_1$ is $C_1$-$C_3$ alkyl, such 3-phenacylpiperidines are prepared by the process which comprises reacting in a suitable solvent a 3-halomethylpiperidine with magnesium to give a 3-piperidylmethylmagnesium halide having the general formula

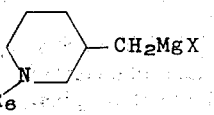

which is condensed with a benzonitrile of the general formula,

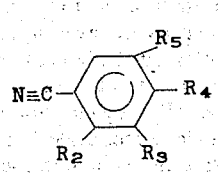

wherein $R_6$ is $C_1$-$C_3$ alkyl; X is chloro, bromo, or iodo; and $R_2$, $R_3$, $R_4$, and $R_5$ are as defined hereinbefore.

The 3-phenacylpiperidines of the present invention are useful as central nervous system depressants or stimulants; some of said 3-phenacylpiperidines also are useful as antiinflammatory agents.

DETAILED DESCRIPTION OF THE INVENTION

Examples of preferred 3-phenacylpiperidines coming within the scope of the present invention include, among others, the following:

3-(4-Fluorophenacyl)piperidine,
3-(2-Fluorophenacyl)piperidine,
1-Methyl-3-phenacylpiperidine,
1-Methyl-3-(4-fluorophenacyl)piperidine,
1-Methyl-3-(3-fluorophenacyl)piperidine,
1-Methyl-3-(2-fluorophenacyl)piperidine,
1-Methyl-3-(4-chlorophenacyl)piperidine,
1-Methyl-3-(3-chlorophenacyl)piperidine,
1-Methyl-3-(2-chlorophenacyl)piperidine,
1-Methyl-3-(4-methylphancyl)piperidine,
1-Methyl-3-(3-methylphenacyl)piperidine,
1-Methyl-3-(2-methylphenacyl)piperidine,
1-Methyl-3-(4-methoxyphenacyl)piperidine,
1-Methyl-3-(4-methylthiophenacyl)piperidine,
1-Methyl-3-[4-(trifluoromethyl)phenacyl]piperidine,
1-Methyl-3-[3-(trifluoromethyl)phenacyl]piperidine,
1-Methyl-3-[2-(trifluoromethyl)phenacyl]piperidine,
1-Methyl-3-(2-chloro-4-fluorophenacyl)piperidine,
1-Methyl-3-(2,5-difluorophenacyl)piperidine, 1-Methyl-3-(3,4-dichlorophenacyl)piperidine,
1-Methyl-3-[2-chloro-5-(trifluoromethyl)phenacyl]-piperidine,
1-Methyl-3-[3,5-bis(trifluoromethyl)phenacyl]-piperidine,
1-Isopropyl-3-(2-fluorophenacyl)piperidine,
1-Allyl-3-(4-fluorophenacyl)piperidine,
1-Allyl-3-(2-fluorophenacyl)piperidine,
1-Cyano-3-(4-fluorophenacyl)piperidine,
1-Cyano-3-(2-fluorophenacyl)piperidine,
1-Carbamoyl-3-(4-fluorophenacyl)piperidine,
1-Carbamoyl-3-(2-fluorophenacyl)piperidine,
and the pharmaceutically-acceptable acid addition salts of basic members thereof.

The most preferred 3-phenacylpiperidines are:
1-Methyl-3-(4-fluorophenacyl)piperidine,
1-Methyl-3-(3-fluorophenacyl)piperidine,
1-Methyl-3-[4-(trifluoromethyl)phenacyl]piperidine,
1-Methyl-3-[3-(trifluoromethyl)phenacyl]piperidine,
1-Methyl-3-(3,4-dichlorophenacyl)piperidine,
1-Allyl-3-(4-fluorophenacyl)piperidine,
1-Carbamoyl-3-(4-fluorophenacyl)piperidine,
and the pharmaceutically-acceptable acid addition salts thereof.

It will be apparent to one skilled in the art that with reference to the general formula for the 3-phenacylpiperidines of the present invention as presented hereinbefore, the preferred 3-phenacylpiperidines are obtained when $R_1$ is selected from the group consisting of hydrogen, methyl, allyl, cyano, and carbamoyl.

"Pharmaceutically-acceptable" acid addition salts are well known to those skilled in the art and in general are formed by reacting in a mutual solvent a stoichiometric amount of a suitable acid with a basic 3-phenacylpiperidine. Such salts should not be substantially more toxic toward mammals than the 3-phenacylpiperidines. While the choice of salt-forming acid is not critical, in some instances a particular acid may result in a salt having special advantages, such as ready solubility, ease of crystallization, and the like. Representative and suitable acids include, among others, the following: hydrochloric, hydrobromic, hydriodic, sulfuric, nitric, phosphoric, formic, acetic, butyric, citric, maleic, tartaric, succinic, benzoic, methanesulfonic, p-toluenesulfonic, and the like.

Certain 3-phenacylpiperidines of the present invention are prepared by the process which comprises reacting in a suitable solvent a 3-halomethylpiperidine with magnesium to give a 3-piperidylmethylmagnesium halide having the general formula

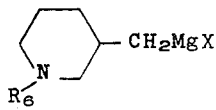

which is condensed with a benzonitrile of the general formula,

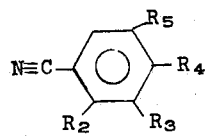

wherein $R_2$, $R_3$, $R_4$, $R_5$, $R_6$, and X are as defined hereinbefore. Preferably, X is chloro; most preferably, X is chloro and $R_6$ is methyl.

The first step of the process of the present invention comprises preparing a 3-piperidylmethylmagnesium halide, from a 3-halomethylpiperidine and magnesium, and in general is carried out in accordance with procedures well known to those skilled in the art.

Some of the 3-halomethylpiperidines employed as starting materials in the first step of the process of the present invention, e.g., 3-chloromethylpiperidine (as the hydrochloride salt), are available commercially. Alternatively, the 3-halomethylpiperidines can be prepared by methods known to those skilled in the art. For example, 3-halomethylpiperidines can be obtained from ethyl nicotinate by the procedure of R. F. Feldkamp, et al., *J. Am. Chem. Soc.*, 74, 3831 (1952), wherein ethyl nicotinate is catalytically reduced to ethyl 3-piperidinecarboxylate. The ethyl 3-piperidinecarboxylate then is N-alkylated by any convenient means; for example, N-methylation is accomplished by repeating the catalytic reduction in the presence of aqueous formaldehyde. The ester group of the resulting ethyl N-alkyl-3-piperidinecarboxylate is reduced to the hydroxymethyl group which then is halogenated to give the desired 3-halomethylpiperidine.

Condensation of the 3-piperidylmethylmagnesium halide with a benzonitrile, the second step in the process of the present invention, is accomplished simply by adding a solution of the desired benzonitrile, in the same solvent used to prepare the 3-piperidylmethylmagnesium halide, to the solution of the Grignard reagent obtained from the first step of the process of the present invention. The addition, which usually results in a mild exotherm, can be carried out portion-wise or all at once. The temperature of the reaction solution can vary from ambient temperature to the reflux temperature of the solvent. Usually, the addition is carried out by adding the benzonitrile solution as a single portion to the Grignard reagent solution at ambient temperature. The resulting solution then is heated at reflux for from about 15 minutes to about three hours, although the reaction time is not critical.

The resulting 3-phenacylpiperidine normally is isolated by the usual work-up procedures. For example, the reaction solution can be diluted with water which, in cases where the reaction solvent is water-miscible, contains dissolved therein an inorganic salt. The organic phase containing the 3-phenacylpiperidine is separated from the aqueous phase which is extracted several times with a suitable organic solvent, such as diethyl ether. The organic phase and extracts are combined and all solvents removed, either by evaporation or distillation at either atmospheric or reduced pressure. The residue then can be recrystallized if a solid or vacuum distilled if a liquid. Alternatively, the residue can be converted to an acid addition salt by well-known procedures.

The benzonitriles employed in the process of the present invention in general are available commercially. Those which are not, however, can be prepared according to known procedures. For example, a benzoic acid is converted to the corresponding benzonitrile by first converting the benzoic acid to the benzoyl halide which is treated with ammonium hydroxide to give the benzamide. The benzamide in turn is dehydrated, with phosphorus pentoxide, for example, to give the desired benzonitrile.

In carrying out the process of the present invention, the use of a 1-methyl-3-halomethylpiperidine is preferred, since the 1-methyl-3-phenacylpiperidine obtained therefrom can be converted to any of a number of other 3-phenacylpiperidines which are both novel and useful by means of the following reaction scheme which employs, by way of illustration only, 1-methyl-3-(4-fluorophenacyl)piperidine as starting material:

agents. In general, such compounds are 1-methyl-3-phenacylpiperidines, of which the following are typical:

1-Methyl-3-(4-fluorophenacyl)piperidine,
1-Methyl-3-(3-fluorophenacyl)piperidine,
1-Methyl-3-(3-chlorophenacyl)piperidine,
1-Methyl-3-(2-chlorophenacyl)piperidine,
1-Methyl-3-(4-methylphenacyl)piperidine,
1-Methyl-3-(3-methylphenacyl)piperidine,

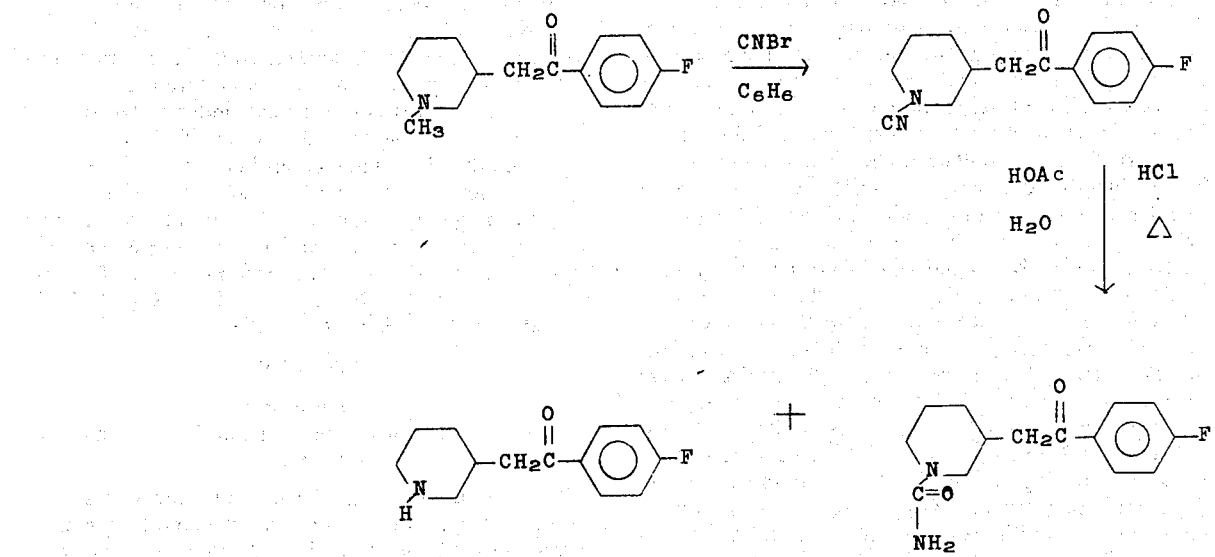

The above reaction scheme generally follows the procedure of E. L. Engelhardt, *J. Med. Chem.*, 11, 325 (1968). Briefly, 1-methyl-3-(4-fluorophenacyl)piperidine in benzene solution is treated at essentially ambient temperature with excess cyanogen bromide under a nitrogen purge. Volatile materials are distilled under reduced pressure and the residue is dissolved in chloroform. The chloroform solution is washed, dried, and filtered. Distillation of the chloroform gives 1-cyano-3-(4-fluorophenacyl)piperidine. Hydrolysis of the cyano compound with hydrochloric acid-containing aqueous acetic acid gives the 1-carbamoyl derivative and the completely hydrolyzed and decarboxylated piperidine derivative (wherein the cyano group effectively is replaced with hydrogen). Increasing the amount of hydrochloric acid employed and increasing reaction time appear to favor complete hydrolysis and decarboxylation.

Most of the compounds of the present invention are active as central nervous system depressants. Such compounds are used in the treatment of such psychosis-induced symptoms as moderate to severe agitation, anxiety, and tension, assaultiveness, delusions, hallucinations, hostility, and hyperactivity. Unexpectedly, however, several of the compounds of the present invention are active as central nervous system stimulants, rather than depressants. The most notable examples of such stimulants are 1-methyl-3-(3-fluorophenacyl)-piperidine, 1-methyl-3-[4-(trifluoromethyl)phenacyl]-piperidine, and 1-methyl-3-(3,4-dichlorophenacyl)-piperidine. Central nervous system stimulants find use in the treatment of minimal brain dysfunction in children and in the treatment of narcolepsy.

As indicated hereinbefore, some of the compounds of the present invention are useful as anti-inflammatory 1-Methyl-3-[4-(trifluoromethyl)phenacyl]piperidine,
1-Methyl-3-[3-(trifluoromethyl)phenacyl[piperidine,
1-Methyl-3-(2-chloro-4-fluorophenacyl)piperidine,
1-Methyl-3-(3,4-dichlorophenacyl)piperidine,
1-Methyl-3-[2-chloro-5-(trifluoromethyl)phenacyl]-piperidine, and pharmaceutically-acceptable acid addition salts thereof.

Anti-inflammatory agents generally are employed in the symptomatic treatment of such inflammatory conditions as rheumatoid arthritis, rheumatoid spondylitis, osteoarthritis, degenerative joint diseases, and the like.

For use as a central nervous system depressant or stimulant, a compound of the present invention or pharmaceutically-acceptable salt thereof is administered to a mammal in an effective amount. Typically, a daily adult dose of from about 0.5 to about 1000 mg is appropriate, either as a single does or, preferably, as two to four divided doses. However, higher doses may be desirable, depending upon the nature of the problem to be alleviated, the severity of symptoms, and the tolerance of the patient to the compound to be administered, among other factors.

In general, a compound of the present invention (including a pharmaceutically-acceptable salt thereof) can be administered either orally or intramuscularly. Preferably, the compound is employed in combination with one or more adjuvants suited to the particular route of administration. Thus, in the case of oral administration, the compound is modified with pharmaceutical diluents or carriers such as lactose, sucrose, starch powder, cellulose, talc, magnesium stearate, magnesium oxide, calcium sulfate, acacia powder, gelatin, sodium alginate, sodium benzoate, stearic acid, and the like. The resulting composition can be formulated as tablets or enclosed in capsules for convenient administration. The compound also can be mixed with a suitable liquid and administered as an elixir, suspension, or the like. In the case of intramuscular administration, the compound conveniently is formulated in saline to provide an injectable liquid solution or suspension. Of course, other adjuvants and modes of administration are known to those skilled in the art. If desired, the pharmaceutical preparations can contain, in addition to a compound of the present invention, one or more pharmacologically-active substances, such as acetylsalicylic acid, α-d-propoxyphene, caffeine, acetaminophen (N-acetyl-p-aminophenol), and the like.

For use as an anti-inflammatory agent, a compound having the desired activity is administered to a mammal at a dosage level of from about 1 to about 50 mg/kg of animal body weight. The administration can be repeated periodically as needed; in accordance with general practice, the compound can be administered every 4 to 6 hours. Administration in general can be carried out orally, parenterally, or in the form of rectal suppositories. Furthermore, preparation of a suitable dosage form can be carried out as already described or according to procedures well known to those skilled in the art.

The present invention will be more fully described, without intending to limit it in any manner, by the following examples which illustrate certain preferred embodiments. In the examples, all temperatures are in degrees centigrade unless otherwise indicated.

EXAMPLE 1

Preparation of 1-methyl-3-piperidylmethylmagnesium chloride

To 12.9 g of magnesium turnings of 50 ml of tetrahydrofuran, under nitrogen, was added several ml of a solution of 71.4 g of 1-methyl-3-chloromethylpiperidine in about 50 ml of tetrahydrofuran. Reaction was initiated by adding about 0.6 ml of ethylene dibromide. The remaining 3-chloromethylpiperidine solution then was added at a rate sufficient to maintain the reaction mixture at reflux temperature, with the concomitant addition of about 100 ml of tetrahdrofuran. When the addition of the 3-chloromethylpiperidine solution was complete, and additional 150 ml of tetrahydrofuran was added. The reaction mixture was warmed to maintain the reaction, after which the reaction mixture was heated at reflux for 1 hour. The reaction mixture then was cooled to ambient temperature and filtered through glass wool to remove excess magnesium.

EXAMPLE 2

Preparation of 1-methyl-3-phenacylpiperidine

1-Methyl-3-piperidylmethylmagnesium chloride was prepared essentially as described in Example 1 from 30.5 g of 1-methyl-3-chloromethylpiperidine. Sufficient tetrahydrofuran was employed to provide a final solution volume of 305 ml. To 114 ml of this final solution of 1-methyl-3-piperidylmethylmagnesium chloride was added 8.9 g of benzonitrile dissolved in about 30 ml of tetrahydrofuran and the resulting solution was heated at reflux for 30 minutes. The reaction solution was cooled and added to 100 ml of water to which 4.5 g of ammonium chloride had been added. A tetrahydrofuran layer separated from the aqueous phase which was extracted with two 75-ml portions of diethyl ether. The resulting extracts and the tetrahydrofuran layer were combined and the resulting organic solution was washed with two 25-ml portions of water and extracted with three 75-ml portions of 3 N hydrochloric acid. The acid extracts were combined and washed with diethyl ether, heated to distill residual diethyl ether and tetrahydrofuran, then heated at reflux for 45 minutes. The resulting hydrochloric acid solution was cooled and made strongly alkaline with 3 N sodium hydroxide. The alkaline solution was extracted with three 100-ml portions of diethyl ether. The extracts were combined, washed with water, dried over anhydrous magnesium sulfate, and filtered. The diethyl ether solution was concentrated under reduced pressure and the residue was vacuum distilled to give 10.7 g of 1-methyl-3-phenacylpiperidine, bp 104°–114°/0.9 mm (collected as three fractions). The infrared and nuclear magnetic resonance spectra of the product were consistent with the assigned structure. The elemental analysis of the second fraction was as follows:

Calculated for $C_{14}H_{19}NO$: C, 77.38; H, 8.81; N, 6.45. Found: C, 77.14; H, 8.89; N, 6.58.

EXAMPLE 3

Preparation of 1-methyl-3-(4-fluorophenacyl)piperidine and maleate salt thereof

To a mixture of 5.0 g of magnesium turnings and 30 ml of tetrahydrofuran were added several crystals of iodine and 0.6 ml of ethylene dibromide. A vigorous reaction ensued. To the reaction mixture were added 20 ml. of tetrahydrofuran and a solution of 12.4 g of 1-methyl-3-chloromethylpiperidine in 30 ml of tetrahydrofuran and the reaction mixture was heated at reflux for 2.5 hours. A solution of 10.2 g of 4-fluorobenzonitrile in 13 ml of tetrahydrofuran was added to the reaction mixture and heating at reflux was resumed and continued for an additional three hours. The reaction mixture was cooled and poured into 150 ml of ten percent aqueous ammonium chloride (w/v); the organic and aqueous phase separated. The aqueous phase was isolated and extracted 4 times with benzene. The organic phase and benzene extracts were combined, washed four times with water and then twice with saturated aqueous sodium chloride, dried over anhydrous calcium sulfate, and filtered. The resulting solution was distilled and the residue was vacuum distilled to give 13.2 g of crude 1-methyl-3-(4-fluorophenacyl)-piperidine, bp 109°–113°/0.3 mm. The crude material was heated on a steam bath with 50 ml of 3 N hydrochloric acid for 15 minutes. The acidic solution was cooled, extracted with diethyl ether, and added to 100 ml of 3 N sodium hydroxide. The resulting alkaline solution was extracted with two 100-ml portions of diethyl ether and one 100-ml portion of benzene. The organic extracts were combined, dried over anhydrous sodium sulfate, and filtered. The organic solvents were distilled and the residue was vacuum distilled at 107°–110°/0.3 mm, then redistilled to give 11.4 g of 1-methyl-3-(4-fluorophenacyl)piperidine, bp 97°–102°/0.09 mm. The following elemental analysis was obtained:

Calculated for $C_{14}H_{18}FNO$: C, 71.46; H, 7.71; N, 5.95 Found: C, 71.33; H, 7.62; N, 5.99.

1-Methyl-3-(4-fluorophenacyl)piperidine, 9.8 g, was dissolved in 3 N sodium hydroxide. The alkaline solution was extracted several times with diethyl ether and the combined extracts were dried over anhydrous magnesium sulfate and filtered. The diethyl ether was distilled under reduced pressure and the residue dissolved in 50 ml of diethyl ether, to which solution was added 7.5 g of maleic acid dissolved in 60 ml of ethyl acetate and 130 ml of diethyl ether. Upon heating the reaction solution, an oil separated which solidified. The solvent was decanted from the solid which was washed with diethyl ether. Drying the solid provided 14.2 g of 1-methyl-3-(4-fluorophenacyl)-piperidine, maleate salt, mp 162.5°–164°. The following elemental analysis was obtained:

Calculated for $C_{18}H_{22}FNO_5$: C, 61.53; H, 6.31; N, 3.99. Found: C, 61.45; H, 6.24; N, 4.00.

EXAMPLE 4

Preparation of
1-methyl-3-(3-fluorophenacyl)piperidine and maleate salt thereof

To a mixture, under nitrogen, of 6.0 g of magnesium turnings and 30 ml of tetrahydrofuran was added about 0.5 ml of ethylene dibromide. The reaction mixture was warmed and a solution of 32.0 g of 1-methyl-3-chloromethylpiperidine in 50 ml of tetrahydrofuran was added. The reaction mixture was warmed again, and about 0.5 ml of ethylene dibromide was added, resulting in vigorous reaction. The reaction mixture was heated at reflux while 260 ml of tetrahydrofuran gradually was added. The reaction mixture was cooled and filtered through glass wool. The final volume of 1-methyl-3-piperidylmethylmagnesium chloride solution was 372 ml.

To 70 ml of the above Grignard reagent solution was added 5.3 g of 3-fluorobenzonitrile. The resulting solution was heated at reflux for one hour, allowed to stand at ambient temperature for 18 hours, and again heated at reflux for 1 hour. The reaction solution was cooled and added to 80 ml of 10 percent aqueous ammonium chloride (w/v). The resulting mixture was extracted with diethyl ether. The diethyl ether solution was washed with water and extracted with 3 N hydrochloric acid. The acidic extract was heated on a steam-bath for 20 minutes, cooled, and made alkaline with ten percent aqueous sodium hydroxide. The resulting alkaline solution was extracted with methylene dichloride. The methylene dichloride was evaporated, the residue was taken up in diethyl ether, and the resulting solution was filtered. The solvent was distilled and the residue vacuum distilled to give 4.9 g of 1-methyl-3-(3-fluorophenacyl)-piperidine, bp 109°–114°/0.25 mm. The following elemental analysis was obtained:

Calculated for $C_{14}H_{18}FNO$: C, 71.46; H, 7.71; N, 5.95. Found: C, 71.50; H, 7.96; N, 6.19.

To a solution of 2.2 g of maleic acid in 40 ml of ethyl acetate was added 3.9 g of 1-methyl-3-(3-fluorophenacyl)-piperidine, followed by the addition of diethyl ether. The oil which separated was induced to crystallize and the resulting crystals were isolated by filtration and recrystallized from ethyl acetate to give 4.4 g of 1-methyl-3-(3-fluorophenacyl)-piperidine, maleate salt. The following elemental analysis was obtained;

Calculated for $C_{18}H_{22}FNO_5$: C, 61.53; H, 6.31; N, 3.99. Found: C, 61.40; H, 6.21; N, 4.07.

EXAMPLE 5

Preparation of
1-methyl-3-(2-fluorophenacy)piperidine and maleate salt thereof

The procedure of Example 4 was repeated, using 70 ml of the same Grignard reagent solution, except that the 3-fluorobenzonitrile was replaced with an equal amount of 2-fluorobenzonitrile, to give 4.6 g of 1-methyl-3-(2-fluorophenacyl)piperidine, bp 108°–114°/0.3 mm. The following elemental analysis was obtained:

Calculated for $C_{14}H_{18}FNO$:
C, 71.46; H, 7.71; N, 5.95.
Found:
C, 71.28; H, 7.98; H, 6.23.

Using an equal amount of 1-methyl-3-(2-fluorophenacyl)piperidine in place of 1-methyl-3-(3-fluorophenacyl)piperidine, the acid addition salt preparation of Example 4 was repeated to give 5.0 g of 1-methyl-3-(2-fluorophenacyl)piperidine, maleate salt, mp 105°–107°. The following elemental analysis was obtained:

Calculated for $C_{18}H_{22}FNO_5$:
C, 61.53; H, 6.31; N, 3.99.
Found:
C, 61.38; H, 6.38; N, 4.02.

EXAMPLE 6

Preparation of
1-methyl-3-(4-chlorophenacyl)piperidine, maleate salt

1-Methyl-3-piperidylmethylmagnesium chloride was prepared essentially as described in Example 4, giving 350 ml of a tetrahydrofuran solution containing 122 mg/ml (calculated) of the Grignard reagent. To 70 ml of this solution, under nitrogen, was added 5.8 g of 4-chlorobenzonitrile dissolved in about 30 ml of tetrahydrofuran. The resulting solution was heated at reflux for one hour, cooled, and added to 100 ml of water containing 2.7 g of ammonium chloride. The organic layer which separated was isolated and the aqueous layer was extracted with two 70-ml portions of diethyl ether. The combined organic layer and diethyl ether extracts were worked up essentially as described in Example 2 to give 4.1 g of crude 1-methyl-3-(4-chlorophenacyl)piperidine, bp 122°–124°/0.15 mm. Approximately 3.3 g of the crude piperidine compound was dissolved in diethyl ether and added to 60 ml of 3:1 ethyl acetate: diethyl ether containing 1.6 g of maleic acid. The mixture was cooled to about 5° and the crystals which had formed were isolated by filtration. The product was recrystallized from acetone/diethyl ether and washed with diethyl ether to give 3.3 g of 1-methyl-3-(4-chlorophenacyl)piperidine, maleate salt, mp 163°–165°. The following elemental analysis was obtained:

Calculated for $C_{18}H_{22}ClNO_5$:
C, 58.78; H, 6.03; N, 3.81.
Found:
C, 58.88; H, 5.78; N, 5.74.

EXAMPLE 7

Preparation of
1-methyl-3-(3-chlorophenacyl)piperidine

The procedure of Example 6 was repeated, except that the concentration of Grignard reagent was 101 mg/ml (calculated), the volume of Grignard reagent solution employed was 136 ml, the 4-chlorobenzonitrile was replaced with 12.1 g of 3-chlorobenzonitrile, the amount of ammonium chloride employed in the work-up procedure was increased to 5.8 g, and the maleate salt procedure was not employed. The yield of 1-methyl-3-(3-chlorophenacyl)piperidine was 13.9 g, bp 121°–128°/0.08 mm. The following elemental analysis was obtained:
Calculated for $C_{14}H_{18}ClNO$:
C, 66.79; H, 7.21; Cl, 14.08; N, 5.56.
Found:
C, 67.07; H, 7.16; Cl, 14.34; N, 5.32.

EXAMPLE 8

Preparation of
1-methyl-3-(2-chlorophenacyl)piperidine and hydrochloride salt thereof The procedure of Example 6 was repeated, except that the 3-chlorobenzonitrile was replaced with the same amount of 2-chlorobenzonitrile and the maleate salt procedure was not employed. The yield of 1-methyl-3-(2-chlorophenacyl)piperidine was 8.5 g, bp 124°–134°/0.3 mm. The following elemental analysis was obtained:
Calculated for $C_{14}H_{18}ClNO$:
C, 66.79; H, 7.21; N, 5.56.
Found:
C, 66.55; H, 7.32; N, 5.27.

1-Methyl-3-(2-chlorophenacyl)piperidine, 24.8 g, was dissolved in 100 ml of diethyl ether. To the resulting solution was added an excess of ethereal hydrogen chloride solution. A heavy oil separated. The solvent was distilled under reduced pressure and acetone was added to the residue. The resulting mixture was heated on a steam-bath until the residue had crystallized. The mixture was cooled, filtered, and thoroughly washed with diethyl ether, giving 26.7 g of 1-methyl-3-(2-chlorophenacyl)piperidine hydrochloride, mp 136°–138°. A small portion of the salt was recrystallized from acetone to give an analytical sample, mp 135.5°–138°, from which the following elemental analysis was obtained:
Calculated for $C_{14}H_{19}Cl_2NO$:
C, 58.34; H, 6.64; Cl, 24.60; N, 4.86.
Found:
C, 58.53; H, 6.80; Cl, 24.46; N, 4.87.

EXAMPLE 9

Preparation of
1-methyl-3-(4-methylphenacyl)piperidine

The procedure of Example 2 was repeated, except that 109 ml of the Grignard reagent solution was employed and the benzonitrile was replaced with 9.5 g of p-tolunitrile. The final distillation of solvent yielded 10.7 g of pale yellow crystals, mp 69°–72°, which were recrystallized from hexane to give 7.1 g of white, crystalline, 1-methyl-3-(4-methylphenacyl)piperidine, mp 70°–74°. The following elemental analysis was obtained:
Calculated for $C_{15}H_{21}NO$:
C, 77.88; H, 9.15; N, 6.05.
Found:
C, 77.58, H, 8.71; N, 6.02.

EXAMPLE 10

Preparation of
1-methyl-3-(3-methylphenacyl)piperidine and maleate salt thereof

The procedure of Example 7 was repeated to prepare 1-methyl-3-(3-methylphenacyl)piperidine, except that the 3-chlorobenzonitrile was replaced with 11.4 g of m-tolunitrile and the amount of ammonium chloride was increased to 6.0 g. The yield of the piperidine compound was 12.7 g, bp 119°–124°/0.1 mm. The following elemental analysis was obtained:
Calculated for $C_{15}H_{21}NO$:
C, 77.88; H, 9.15; N, 6.05.
Found:
C, 77.74; H, 8.95; N, 6.23.

The 1-methyl-3-(3-methylphenacyl)piperidine obtained above was dissolved in about 100 ml of diethyl ether. The resulting solution was added to a diethyl ether solution of maleic acid. The solvent was decanted from the resulting solid which was taken up in hot acetone. The resulting solution was cooled and diluted with diethyl ether. The crystals which formed were isolated by filtration, washed with diethyl ether, and recrystallized from acetone/diethyl ether to give 12.6 g of 1-methyl-3-(3-methylphenacyl)piperidine, maleate salt, mp 92°–94°. The following elemental analysis was obtained:
Calculated for $C_{19}H_{25}NO_5$:
C, 65.69; H, 7.25; N, 4.03.
Found:
C, 65.82; H, 7.42; N, 3.94.

EXAMPLE 11

Preparation of
1-methyl-3-(4-methoxyphenacyl)piperidine, maleate salt

The procedure of Example 6 was repeated, using 82 ml of the same Grignard reagent solution, except that the 4-chlorobenzonitrile was replaced with 6.2 g of anisonitrile. The yield of crude 1-methyl-3-(4-methoxyphenacyl)piperidine was 7.3 g, bp 134°–138°/0.1 mm. Conversion of the piperidine compound to the maleate salt utilized 4.4 g of maleic acid with appropriate increases in solvent volumes. The crude salt thus obtained, 10.7 g, mp 91°–94°, was recrystallized to give 9.5 g of 1-methyl-3-(4-methoxyphenacyl)piperidine, maleate salt, mp 89°–92°. The following elemental analysis was obtained:
Calculated for $C_{19}H_{25}NO_6$:
C, 62.80; H, 6.93; N, 3.85
Found:
C, 62.62; H, 7.20; N, 3.66

EXAMPLE 12

Preparation of
1-methyl-3-(4-methylthiophenacyl)piperidine

1-Methyl-3-piperidylmethylmagnesium chloride was prepared essentially as described in Example 4, using 2.7 g of magnesium turnings and 14.0 g of 1-methyl-3-chloromethylpiperidine. The Grignard reagent thus obtained was employed to prepare 1-methyl-3-(4-methylthiophenacyl)piperidine essentially as described in Example 2, except that the benzonitrile was replaced with 14.2 g of 4-methylthiobenzonitrile. Final distillation of solvent yielded 15.3 g of oil which recrystallized upon standing. The solid was recrystallized from diethyl ether/hexane to give 11.2 g of 1-methyl-3-(4-methylthiophenacyl)piperidine, mp 61.5°–62.5°. The following elemental analysis was obtained:

Calculated for $C_{15}H_{21}NOS$:
C, 68.40; H, 8.04; N, 5.32; O, 6.07; S, 12.17.
Found:
C, 68.55; H, 8.25; N, 5.22; O, 6.29; S, 11.93.

EXAMPLE 13

Preparation of
1-methyl-3-[4-(trifluoromethyl)phenacyl]piperidine and maleate salt thereof The procedure of Example 5 was repeated, except that the 2-fluorobenzonitrile was replaced with 7.1 g of 4-(trifluoromethyl)benzonitrile, to give 6.0 g of 1-methyl-3-[4-(trifluoromethyl)phenacyl]piperidine, bp 116°–120°/0.3 mm. The following elemental analysis was obtained:

Calculated for $C_{15}H_{18}F_3NO$:
C, 63.15; H, 6.63; N, 4.91.
Found:
C, 63.02; H, 6.60; N, 5.03.

Preparation of the maleate salt employed 5.0 g of the piperidine compound, yielding 6.1 g of 1-methyl-3-[4-trifluoromethyl)phenacyl]piperidine, maleate salt, mp 126.5°–128°. The following elemental analysis was obtained:

Calculated for $C_{19}H_{22}F_3NO_5$:
C, 56.86; H, 5.52; N, 3.49.
Found:
C, 57.14; H, 5.71; N, 3.32.

EXAMPLE 14

Preparation of
1-methyl-3-[3-(trifluoromethyl)phenacyl]piperidine

The procedure of Example 6 was repeated, except that the concentration of Grignard reagent was 103 mg/ml (calculated), the volume of Grignard reagent employed was 103 ml, the 4-chlorobenzonitrile was replaced with 10.8 g of 3-(trifluoromethyl)-benzonitrile, the amount of ammonium chloride employed in the work-up procedure was increased to 3.5 g, and the maleate salt procedure was not employed. Furthermore, the final crude material, prior to vacuum distillation, was chromatographed on a silica gel golumn with chloroform as eluant. The column then was flushed with 9:1 chloroform:methanol. The appropriate eluant fractions and column flushing solvent mixture were combined and distilled in vacuo, leaving 8.6 g of an oil. The oil was vacuum distilled twice to give 4.3 g of 1-methyl-3-[3-(trifluoromethyl)phenacyl]piperidine, bp 105°–106.5°/0.09 mm (third and final fraction from second distillation). The following elemental analysis was obtained (on said third fraction):

Calculated for $C_{15}H_{18}F_3NO$:
C, 63.15; H, 6.36; N, 4.91.
Found:
C, 63.02; H, 6.59; N, 5.21.

EXAMPLE 15

Preparation of
1-methyl-3-(2-chloro-4-fluorophenacyl)piperidine and maleate salt thereof The procedure of Example 6 was repeated, except that the concentration of Grignard reagent was 79 mg/ml (calculated), the volume of Grignard reagent employed was 77 ml, the 4-chlorobenzonitrile was replaced with 5.3 g of 2-chloro-4-fluorobenzonitrile, the amount of ammonium chloride employed in the work-up procedure was reduced to 2.5 g, and the pure piperidine compound was isolated prior to the preparation of the maleate salt thereof. The yield of 1-methyl-3-(2-chloro-4-fluorophenacyl)piperidine was 4.8 g, bp 117.5°–120°/0.2 mm. The following elemental analysis was obtained:

Calculated for $C_{14}H_{17}ClFNO$:
C, 62.34; H, 6.35; Cl, 13.14; N, 5.19.
Found:
C, 62.04; H, 6.56; Cl, 13.12; N, 5.48.

The yield of 1-methyl-3-(2-chloro-4-fluorophenacyl)piperidine, maleate salt, was 6.2 g, mp 117°–118.5°. The following elemental analysis was obtained on a recrystallized portion:

Calculated for $C_{18}H_{21}ClFNO_5$:
C, 56.04; H, 5.49; Cl, 9.19; N, 3.63.
Found:
C, 56.22; H, 5.63; Cl, 9.48; N, 3.80.

EXAMPLE 16

Preparation of
1-methyl-3-(3,4-dichlorophenacyl)piperidine

The procedure of Example 3 was repeated, except that the Grignard reagent was prepared from 2.0 g of magnesium turnings and 10.3 g of 1-methyl-3-chloromethylpiperidine and the use of iodine was omitted, the 4-fluorobenzonitrile was replaced with 13.3 g of 3,4-dichlorobenzonitrile, the ammonium chloride solution was replaced with 100 ml of water containing 8 of ammonium chloride, the work-up procedure generally followed that described in Example 2, and the maleate salt procedure was not employed. The crude product, 16.2 g, was recrystallized first from acetone and then from hexane to give 7.4 g of 1-methyl-3-(3,4-dichlorophenacyl)piperidine, mp 69°–71°. The following elemental analysis was obtained:

Calculated for $C_{14}H_{17}Cl_2NO$:
C, 58.75; H, 5.99; Cl, 24.77; N, 4.89; O, 5.59.
Found:
C, 58.90; H, 6.13; Cl, 24.75; N, 4.97; O, 5.64.

EXAMPLE 17

Preparation of
1-methyl-3-[2-chloro-5-(trifluoromethyl)phenacyl]-piperidine and maleate salt thereof The procedure of Example 15 was repeated, using 137 ml of the same Grignard reagent solution, except that the 2-chloro-4-fluorobenzonitrile was replaced with 12.5 g of 2-chloro-5-(trifluoromethyl)benzonitrile, and the amount of ammonium chloride employed in the work-up procedure was increased to 4.0 g. The yield of 1-methyl-3-[2-chloro-5-(trifluoromethylphenacyl]piperidine was 7.3 g, bp 134°–136.5°/0.1 mm. The following elemental analysis was obtained:

Calculated for $C_{15}H_{17}ClF_3NO$: C, 56.34; H, 5.36; Cl, 11.09; N, 4.38. Found: C, 55.28; H, 5.80; Cl, 11.36; N, 5.39.

The yield of 1-methyl-3-[2-chloro-5-(trifluoromethyl)phenacyl]piperidine, maleate salt, was 7.5 g, mp 112°–115°. The following elemental analysis was obtained:

Calculated for $C_{19}H_{21}ClF_3NO_5$: C, 52.36; H, 4.86; Cl, 8.13; N, 3.21. Found: C, 52.60; H, 5.06; Cl, 8.42; N, 3.25.

EXAMPLE 18

Preparation of 1-methyl-3-[3,5-bis(trifluoromethyl)phenacyl]piperidine

The procedure of Example 17 was repeated, except that the volume of Grignard reagent employed was 118 ml, the 2-chloro-5-(trifluoromethyl)benzonitrile was replaced with 12.5 g of 3,5-bis(trifluoromethyl)benzonitrile, the amount of ammonium chloride employed in the work-up procedure was reduced to 3.5 g, and the maleate salt procedure was not carried out. The yield of crude 1-methyl-3-[3,5-bis(trifluoromethyl)phenacyl]piperidine was 6.1 g, a small portion of which was vacuum distilled to give an analytical sample, bp 95°/0.2 mm. The following elemental analysis was obtained:

Calculated for $C_{16}H_{17}F_6NO$: C, 54.39; H, 4.85; N, 3.96. Found: C, 54.11; H, 5.01; N, 3.86.

EXAMPLE 19

Preparation of 1-cyano-3-(4-fluorophenacyl)piperidine

To a solution of 13.2 g of cyanogen bromide in 200 ml of benzene at 10° was added, under nitrogen and during a ten-minute period, a solution of 25.2 g of 1-methyl-3-(4-fluorophenacyl)piperidine (Example 3) in 100 ml of benzene. The reaction solution then was agitated at ambient temperature for 16 hours. Volatile materials were distilled under reduced pressure, the residue was taken up in chloroform, and the resulting solution was washed successively with water, 3 N hydrochloric acid, and water, and dried over anhydrous sodium sulfate. The chloroform was distilled to give 23.0 g of an oil. Hexane was added to the oil and the hexane then was decanted from the residue and distilled to give 1-cyano-3-(4-fluorophenacyl)piperidine. Infrared and mass spectrographic analyses were consistent with the assigned structure.

EXAMPLE 20

Preparation of 1-cyano-3-(2-fluorophenacyl)piperidine

The procedure of Example 19 was repeated, using 9.5 g of cyanogen bromide, 19.3 g of 1-methyl-3-(2-fluorophenacyl)piperidine (Example 5), and an additional 130 ml of benzene. The final residue, 16.3 g, was vacuum distilled to give 13.5 g of 1-cyano-3-(2-fluorophenacyl)piperidine, bp 190°–195°/0.5 mm. The following elemental analysis was obtained:

Calculated for $C_{14}H_{15}FN_2O$: C, 68.28; H, 6.14; N, 11.37. Found: C, 67.90; H, 6.33; N, 11.68.

EXAMPLE 21

Preparation of 1-carbamoyl-3-(4-fluorophenacyl)piperidine

1-Cyano-3-(4-fluorophenacyl)piperidine (Example 19), 21.5 g, was dissolved in a mixture of 150 ml of glacial acetic acid, 30 ml of concentrated aqueous hydrochloric acid, and 70 ml of water. The resulting solution, under a nitrogen atmosphere, was heated on a steam-bath for 16 hours. The reaction solution was distilled under reduced pressure, the residue was diluted with water, and the resulting solution was made alkaline with 3 N sodium hydroxide. Upon extracting the alkaline aqueous solution with ethyl ether, solid precipitated and was isolated by filtration and washed with ether. The solid, 6.7 g, was recrystallized once from aqueous acetone and then four times from acetone/diethyl ether, to give 1-carbamoyl-3-(4-fluorophenacyl)piperidine, mp 136°–137.5°. The following elemental analysis was obtained:

Calculated for $C_{14}H_{17}FN_2O_2$: C, 63.62; H, 6.48; F, 7.19; N, 10.60. Found: C, 63.58; H, 6.66; F, 7.48; N, 10.64.

EXAMPLE 22

Preparation of 3-(4-fluorophenacyl)piperidine, maleate salt

The procedure of Example 19 was repeated to give 19 g of crude 1-cyano-3-(4-fluorophenacyl)piperidine, except that 5.4 g of cyanogen bromide, 10.0 g of 1-methyl-3-(4-fluorophenacyl)piperidine (Example 3), and 110 ml of benzene were employed and the addition was carried out at ambient temperature over a 45-minute period. The crude cyanopiperidine was hydrolyzed as described in Example 21, using as the hydrolysis mixture a solution consisting of 80 ml of glacial acetic acid, 40 ml of water, and 20 ml of concentrated hydrochloric acid; hydrolysis time was increased to 19 hours. The final residue was taken up in diethyl ether and combined with a solution of 2.6 g of maleic acid in 200 ml of diethyl ether. An oil separated which crystallized upon standing. The solid, 5.5 g, was recrystallized 3 times from acetone/diethyl ether to give 3-(4-fluorophenacyl)piperidine, maleate salt, mp 131°–132°. The following elemental analysis was obtained:

Calculated for $C_{17}H_{20}FNO_5$: C, 60.53; H, 5.98; N, 4.15. Found: C, 60.56; H, 6.12; N, 4.30.

EXAMPLE 23

Preparation of 1-carbamoyl-3-(2-fluorophenacyl)piperidine hydrochloride

1-Methyl-3-(2-fluorophenacyl)piperidine was prepared essentially as described in Example 5. The 1-cyano analog was prepared from the 1-methyl compound by the procedure of Example 20. The crude 1-cyano-3-(2-fluorophenacyl)piperidine, 66.4 g, was dissolved in a mixture of 470 ml of glacial acetic acid, 150 ml of concentrated hydrochloric acid, and 150 ml of water. The resulting solution, under nitrogen, was heated on a steam-bath for 17.5 hours. The reaction solution was worked up essentially as described in Example 21, except that an oil separated during the diethyl ether extraction. The oil and diethyl ether extracts were combined and diethyl ether was distilled. The residue was subjected to the hydrolysis procedure, except that the volume of glacial acetic acid was reduced to 400 ml and hydrolysis time was reduced to 15.75 hours. Work-up procedure was the same. During diethyl ether extraction, an oil again separated. The addition of chloroform to the multilayer mixture caused a precipitate to form in both the aqueous and chloroform layers. Solid also formed in the oil layer which remained insoluble. The solid in the chloroform layer was isolated by filtration and recrystallized three times from acetone/diethyl ether to give 1-carbamoyl-3-(2-fluorophenacyl)piperidine hydrochloride, mp 125°–128°. The following elemental analysis was obtained:

Calculated for $C_{14}H_{18}ClFN_2O_2$: C, 55.91; H, 6.03; Cl, 11.79; N, 9.31. Found: C, 56.10; H, 6.07; Cl, 11.56; N, 9.43.

EXAMPLE 24

Preparation of 1-allyl-3-(4-fluorophenacyl)piperidine

To 2.3 g of 3-(4-fluorophenacyl)piperidine (Example 22) in tetrahydrofuran was added 2.1 g of potassium carbonate and 0.9 ml of 3-chloropropene. The reaction mixture was agitated at room temperature for 91 hours and then concentrated in vacuo. The residue was taken up in water and extracted with diethyl ether. The diethyl ether was extracted twice with 30-ml portions of 3 N hydrochloric acid. The acidic extracts were combined, washed with diethyl ether, and made alkaline with 3 N sodium hydroxide. The alkaline solution was extracted twice with 40 ml portions of diethyl ether. All diethyl ether extracts were combined, washed with water, and distilled under reduced pressure, giving 2.1 g of an oil. The oil was dissolved in chloroform and chromatographed over silica gel. The eluant was chloroform initially, to which one percent methanol later was added (about half way through the procedure). The first 11 fractions were combined (2865 ml out of 3465 ml) and concentrated in vacuo to yield 1.3 g of an oil which, upon cooling, solidified. The solid was identified by nuclear magnetic resonance analysis and the following elemental analysis as 1-allyl-3-(4-fluorophenacyl)piperidine:

Calculated for $C_{16}H_{20}FNO$: C, 73.54; H, 7.71; N, 5.36. Found: C, 73.34; H, 7.74; N, 5.17.

What is claimed is:

1. A compound selected from the group consisting of 1-methyl-3-(4-fluorophenacyl)piperidine, 1-methyl-3-(3-fluorophenacyl)piperidine, 1-methyl-3-[4-(trifluoromethyl)phenacyl]piperidine, 1-methyl-3-[3-(trifluoromethyl)phenacyl]piperidine, 1-methyl-3-(3,4-dichlorophenacyl)piperidine, and the pharmaceutically-acceptable acid addition salts thereof.

2. The compound of claim 1, wherein said compound is 1-methyl-3-(4-fluorophenacyl)piperidine or a pharmaceutically-acceptable acid addition salt thereof.

3. The compound of claim 1, wherein said compound is 1-methyl-3-(3-fluorophenacyl)piperidine or a pharmaceutically-acceptable acid addition salt thereof.

4. The compound of claim 1, wherein said compound is 1-methyl-3-[4-(trifluoromethyl)phenacyl]piperidine or a pharmaceutically-acceptable acid addition salt thereof.

5. The compound of claim 1, wherein said compound is 1-methyl-3-[3-(trifluoromethyl)phenacyl]piperidine or a pharmaceutically-acceptable acid addition salt thereof.

6. The compound of claim 1, wherein said compound is 1-methyl-3-(3,4-dichlorophenacyl)piperidine or a pharmaceutically-acceptable acid addition salt thereof.

* * * * *